United States Patent [19]

Miyadera et al.

[11] Patent Number: 4,613,595
[45] Date of Patent: Sep. 23, 1986

[54] PENEM DERIVATIVES, AND COMPOSITION CONTAINING THEM

[75] Inventors: Tetsuo Miyadera; Yukio Sugimura; Toshihiko Hashimoto; Teruo Tanaka; Kimio Iino; Tomoyuki Shibata; Shinichi Sugawara, all of Hiromachi, Japan

[73] Assignee: Sankyo Company Limited, Tokyo, Japan

[21] Appl. No.: 494,570

[22] Filed: May 13, 1983

[30] Foreign Application Priority Data

May 14, 1982 [JP] Japan .................................. 57-81067

[51] Int. Cl.[4] .................. C07D 499/00; A61K 31/425
[52] U.S. Cl. ...................................... 514/195; 514/192; 540/310
[58] Field of Search ................ 260/245.2 R, 245.2 T; 424/270; 514/192, 195

[56] References Cited

U.S. PATENT DOCUMENTS

| | | | |
|---|---|---|---|
| 4,323,569 | 4/1982 | Baxter | 260/245.2 T |
| 4,386,030 | 5/1983 | Christensen et al. | 260/245.2 R |
| 4,435,412 | 3/1984 | Girjavallabhan et al. | 424/270 |
| 4,517,124 | 5/1985 | Broom | 260/245.2 R |

FOREIGN PATENT DOCUMENTS 0176988 10/1982 Japan .

*Primary Examiner*—Nicholas S. Rizzo
*Attorney, Agent, or Firm*—Frishauf, Holtz, Goodman & Woodward

[57] ABSTRACT

Compounds of formula (I):

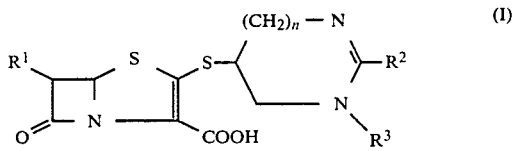

(wherein
$R^1$ represents a $C_1$–$C_4$ alkyl or $C_1$–$C_3$ alpha-hydroxyalkyl group;
$R^2$ represents a hydrogen atom, a substituted or unsubstituted alkyl group or a cycloalkyl group;
$R^3$ represents a hydrogen atom or an alkyl group; and n is 1 or 2) and their salts and esters have valuable antibiotic activity and can be used for the treatment of diseases caused by a wide range of pathogenic microorganisms.

18 Claims, No Drawings

PENEM DERIVATIVES, AND COMPOSITION CONTAINING THEM

BACKGROUND TO THE INVENTION

The present invention relates to a series of new penem compounds exhibiting valuable antibiotic activity, to a process for preparing these compounds and to antibiotic compositions containing the compounds as the active agent.

The penicillins form a well known class of antibiotics, which have found considerable use in human and animal therapy for years. Chemically, the penicillins have in common a beta-lactam structure, commonly referred to as "penam", which may be represented by the following formula

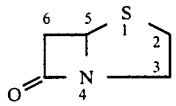

The structure of many valuable penicillin derivatives has a double bond between the 2- and 3-positions and the resulting structure is known as "penem" and forms the basis for the semi-systematic nomenclature of the penicillins. This semi-systematic system of nomenclature is employed herein.

The basic "penem" structure contains atoms or groups of atoms attached to the carbon atoms at the 2- and 6-positions and will normally contain a carboxy group or derivative thereof (e.g. salt or ester) attached to the carbon atom at the 3-position. Differences in the activities, potencies and other properties of the various penicillin derivatives are dictated by the various groups attached to these positions, but the way in which such groups affect the penicillin derivatives has not been elucidated.

U.S. Pat. No. 4,260,618 discloses a series of penem derivatives having a heterocyclic-substituted thio group at the 2-position.

We have now discovered a series of novel penem derivatives having, at the 2-position, a heterocyclic-substituted thio group in which the heterocyclic ring has two nitrogen atoms, i.e. differing substantially in structure from those disclosed in U.S. Pat. No. 4,260,618. These penem derivatives have been found to have comparable antibacterial activities with and better biological and chemical stability tnan, for example, thienamycin which is one of the most potent and valuable beta-lactam antibiotics currently available.

BRIEF SUMMARY OF INVENTION

The novel compounds of the present invention may be represented by the formula (I);

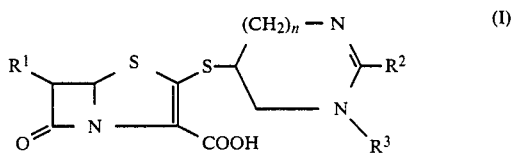

(in which:
$R^1$ represents a $C_1$–$C_4$ alkyl group or a $C_1$–$C_3$ alpha-hydroxyalkyl group;
$R^2$ represents a hydrogen atom, an alkyl group, a cycloalkyl group or an alkyl group having one or more $C_1$–$C_4$ alkoxy, cyano, alkoxycarbonyl or halogen substituents;
$R^3$ represents a hydrogen atom or an alkyl group; and n is 1 or 2)
and pharmaceutically acceptable salts and esters thereof.

The invention also provides an antibiotic composition comprising an antibiotic in admixture with a pharmaceutically acceptable carrier or diluent, wherein the antibiotic comprises at least one compound of formula (I) or salt or ester thereof.

DETAILED DESCRIPTION OF INVENTION

Where $R^1$ presents a $C_1$–$C_4$ alkyl group, this may be a straight or branched chain group, i.e. a methyl, ethyl, propyl, isopropyl, butyl, isobutyl, sec-butyl or t-butyl group. Where $R^1$ represents a $C_1$–$C_3$ alpha-hydroxyalkyl group, this may be a hydroxymethyl, 1-hydroxyethyl, 1-hydroxypropyl or 1-hydroxy-1-methylethyl group; it is preferably a $C_2$ or $C_3$ alpha-hydroxyalkyl group and is most preferably a 1-hydroxyethyl group.

Where $R^2$ represents an alkyl group, this is preferably a lower alkyl group having from 1 to 4 carbon atoms, i.e. a methyl, ethyl, propyl, isopropyl, butyl, isobutyl, sec-butyl or t-butyl group. Where $R^2$ represents a cycloalkyl group, it is preferably a cyclopropyl, cyclobutyl, cyclopentyl, cyclohexyl or cycloheptyl group. Where $R^2$ represents a $C_1$–$C_4$ alkoxy-substituted alkyl group, it is preferably a methoxymetnyl, ethoxymethyl, propoxymethyl, isopropoxymethyl, 1-methoxyethyl or 2-methoxyethyl group. Where it is a cyano-substituted alkyl group, it is preferably a cyanometnyl, 1-cyanoethyl, 2-cyanoethyl, 2-cyanopropyl or 1-methyl-2-cyanoethyl group. Where $R^2$ represents an alkoxycarbonyl-substituted alkyl group, the alkoxy and alkyl groups thereof are preferably $C_1$–$C_4$ groups and it is preferably a methoxycarbonylmethyl, ethoxycarbonylmethyl, 2-methoxycarbonylethyl or 2-ethoxycarbonylpropyl group. Where $R^2$ represents a halogen-substituted alkyl group, it is preferably a $C_1$–$C_4$ group, e.g. a 2-fluoroethyl, 2-fluoropropyl, 2-fluoro-1-metnylethyl, trifluoromethyl or 2,2,2-trifluoroethyl group.

$R^2$ preferably represents a hydrogen atom, a $C_1$–$C_3$ alkyl group or a ($C_1$–$C_2$ alkoxy)-($C_1$–$C_2$ alkyl) group, most preferably a hydrogen atom, a methyl group, an ethyl group or a methoxymethyl group.

Where $R^3$ represents an alkyl group, this is preferably a lower alkyl group having from 1 to 4 carbon atoms and may be a straight or branched chain group, i.e. a methyl, ethyl, propyl, isopropyl, butyl, isobutyl, sec-butyl or t-butyl group. $R^3$ preferably represents a hydrogen atom or a methyl group.

The integer represented by n may be 1 or 2 and is preferably 1.

The compounds of the invention, being acids, will, of course, form salts and the pharmaceutically acceptable salts form part of the present invention. Suitable salts include salts with metals, such as lithium, sodium, potassium, calcium or magnesium, the ammonium salts and salts with organic amines, such as the cyclohexylammonium, diisopropylammonium or triethylammonium salts. The sodium and potassium salts are preferred.

The compounds also form esters and pharmaceutically acceptable esters form part of the present invention. The esters are preferably lower aliphatic acyloxymethyl, lower 1-alkoxycarbonyloxyethyl or (5-methyl-2-oxo 1,3-dioxolen-4-yl)methyl esters. The lower aliphatic acyloxymethyl groups preferably have from 2 to 5 carbon atoms in tne acyl moiety and examples of such groups include the acetoxymethyl, propionyloxymethyl, butyryloxymethyl, isobutyryloxymethyl and pivaloyloxymethyl groups, of which the pivaloyloxymethyl group is preferred. The lower 1-alkoxycarbonyloxyethyl groups preferably have from 1 to 4 carbon atoms in the lower alkoxy moiety and examples include the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl groups. The esters employed are preferably physiologically active; specifically, we prefer esters which undergo hydrolysis in the body of the patient (normally human) to liberate the free acid, which then serves as the effective and active therapeutic substance. It is for this reason that the lower aliphatic acyloxymethyl, lower 1-alkoxycarbonyloxyethyl and (5-methyl-2-oxo-1,3-dioxolen-4-yl)methyl esters are particularly preferred, as these are well known to hydrolyze in the human body to liberate the free acid.

However, the free acid or a pharmaceutically acceptable salt thereof is preferred.

Examples of preferred compounds of the present invention appear in the following list:

1. 2-(2-cyanomethyl-3,4,5,6-tetrahydropyrimidin-5-ylthio)-6-(1-hydroxyethyl)-2-penem-3-carboxylic acid
2. 6-isopropyl-2-(2-methyl-3,4,5,6-tetrahydropyrimidin-5-ylthio)-2-penem-3-carboxylic acid
3. 6-(1-hydroxyethyl)-2-(3,4,5,6-tetrahydropyrimidin-5-ylthio)-2-penem-3-carboxylic acid
4. 6-(1-hydroxyethyl)-2-(2-methyl-3,4,5,6-tetrahydropyrimidin-5-ylthio)-2-penem-3-carboxylic acid
5. 6-(1-hydroxyethyl)-2-(2-methoxymethyl-3-4,5,6-tetrahydropyrimidin-5-ylthio)-2-penem-3-carboxylic acid
6. 6-(1-hydroxyethyl)-2-(4,5,6,7-tetrahydro-2H-1,3-diazepin-5-ylthio)-2-penem-3-carboxylic acid
7. 6-(1-hydroxyethyl)-2-(2-methyl-4,5,6,7-tetrahydro-2H-1,3-diazepin-5-ylthio)-2-penem-3-carboxylic acid
8. Pivaloyloxymethyl 6-(1-hydroxyethyl)-2-(2-methyl-3,4,5,6-tetrahydropyridimidin-5-ylthio)-2-penem-3-carboxylate
9. 6-(1-hydroxyethyl)-2-(2-methoxycarbonylmethyl-3,4,5,6-tetrahydropyrimidin-5-ylthio)-2-penem-3-carboxylic acid
10. 6-(1-hydroxyethyl)-2-(2-trifluoromethyl-3,4,5,6-tetrahydropyrimidin-5-ylthio)-2-penem-3-carboxylic acid
11. 2-[2-(2-fluoroethyl)-3,4,5,6-tetrahydropyrimidin-5-ylthio)-6-(1-hydroxyethyl)]-2-penem-3-carboxylic acid
12. 2-(2-ethyl-3,4,5,6-tetrahydropyrimidin-5-ylthio)-6-(1-hydroxyethyl)-2-penem-3-carboxylic acid
13. 6-(1-hydroxyethyl)-2-(2-isopropyl-3,4,5,6-tetrahydropyrimidin-5-ylthio)-2-penem-3-carboxylic acid
14. 2-(2-cyclopentyl-3,4,5,6-tetrahydropyrimidin-5-ylthio)-6-(1-hydroxyethyl)-2-penem-3-carboxylic acid
15. 6-ethyl-2-(2-methoxymethyl-3,4,5,6-tetrahydropyrimidin-5-ylthio)-2-penem-3-carboxylic acid
16. 2-(2,3-dimethyl-3,4,5,6-tetrahydropryimidin-5-ylthio)-6-(1-hydroxyethyl)-2-penem-3-carboxylic acid Of the above, the most preferred are compounds No. 3, 4, 5, and 12 and their salts.

The compounds of the present invention may exist in the form of various optical isomers, because of the presence of various asymmetric carbon atoms, and may also exist in the form of various geometric isomers. All of the isomers are represented by a single, plane formula in the specification and claims; however, the present invention contemplates the use of either the individual isomers or of mixtures, e.g. racemates, thereof. The preferred compounds are those having the (5R,6S) configuration and, where $R^1$ represents an alpha-hydroxyalkyl group, the hydroxy group is preferably in the R-configuration The compounds of the present invention may be prepared by either of the following Methods;

Method A

Compounds of the invention may be prepared as illustrated by the following reaction scheme;

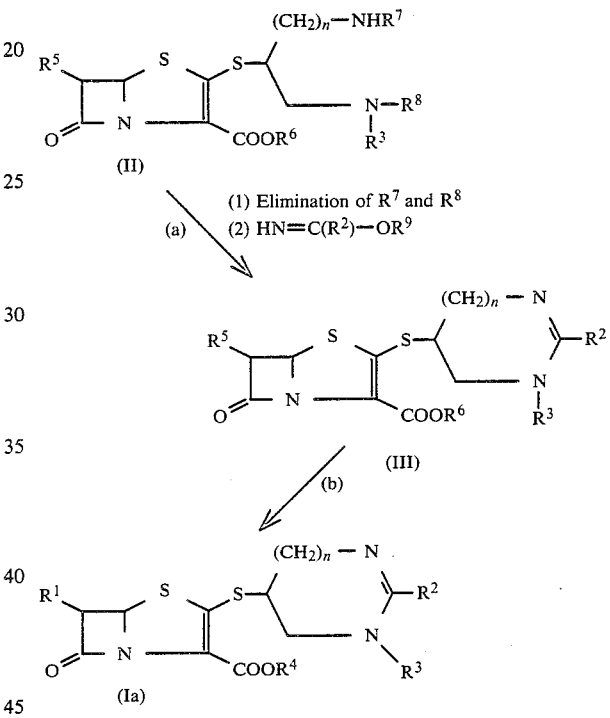

In the above formulae, $R^1$, $R^2$, $R^3$ and n are as defined above. $R^4$ represents a hydrogen atom or an ester group, preferably a lower aliphatic acyloxymethyl group, a lower 1-alkoxycarbonyloxyethyl group or a (5-methyl-2-oxo-1,3-dioxolen-4-yl)methyl group. $R^5$ represents an alkyl group, a $C_1$–$C_3$ alpha-hydroxyalkyl group or a $C_1$–$C_3$ alpha-hydroxyalkyl group in which the hydroxy group has been protected (for example an alpha-acyloxyalkyl, alpna-alkylsulphonyloxyalkyl, alpha-arylsulphonyl-oxyalkyl or alphatrialkylsilyloxyalkyl group). $R^6$ represents a hydrogen atom or a carboxy-protecting group, which may or may not be the same as any ester group represented by $R^4$, but which will normally be different. $R^7$ and $R^8$ represent amino-protecting groups. $R^9$ represents a lower, preferably $C_1$–$C_4$, alkyl group.

In step (a) of this reaction, tne compound of formula (II) is first subjected to a reaction to eliminate the amino-protecting groups represented by $R^7$ and $R^8$. This reaction may be carried out by conventional means and the nature of the reaction employed will, of course, depend upon the particular amino-protecting groups chosen. For example, where the protecting groups are aralkyloxycarbonyl groups (for example benzyloxycarbonyl or p-nitrobenzyloxycarbonyl), this elimination is preferably effected by catalytic reduction using platinum or palladium-on-charcoal as a catalyst; occasionally, this reaction may also lead to elimination of the hydroxy-protecting group if $R^5$ represents a protected alpha-hydroxyalkyl group and/or elimination of the carboxy-protecting group represented by $R^6$. The resulting product may then be reacted, without any intermediate isolation, with the iminoether of formula $HN=C(R^2)-OR^9$. In the iminoether, $R^9$ represents a lower alkyl group, preferably a methyl group, and the iminoether may be employed as such or in the form of an acid addition salt.

Both parts of step (a) are preferably effected in the presence of an aqueous solvent, the nature of which is not critical to the process of the invention, although we prefer to employ an aqueous phosphate buffer maintained at a pH value of from 7 to 9, particularly about 8. The reaction is preferably effected at a relatively low temperature e.g., from 0° C. to ambient temperature and the time required for the reaction will vary, depending upon the reaction temperature, but it will usually be from 10 minutes to 2 hours.

After completion of the reactions of step (a), the desired compound (III) may be recovered from the reaction mixture by conventional means and, if necessary, further purified by such conventional techniques as recrystallization, preparative thin layer chromatography or column chromatography.

Where, in the compound of formula (II), $R^5$ represents an alkyl group or an alpha-hydroxyalkyl group and $R^7$ represents a hydrogen atom or a desired ester group, or where the reaction employed to eliminate the amino-protecting groups represented by $R^7$ and $R^8$ also had the effect of eliminating any hydroxy-protecting group in a protected alpha-hydroxyalkyl group represented by $R^5$ or had the effect of eliminating any carboxy-protecting group represented by $R^6$, then the resulting compound of formula (III) may be the desired final product.

However, where $R^5$ in the compound of formula (III) represents a protected alpha-hydroxyalkyl group and/or $R^6$ represents a carboxy-protecting group, tnen it will be desired to effect step (b) to eliminate the unwanted protecting group or groups. The nature of the reaction or reactions employed to remove undesired protecting groups will, of course, vary depending upon the nature of the protecting group in question and, in some cases, it may be possible to eliminate two protecting groups simultaneously by a single reaction whereas, in other cases, it may be desired to eliminate two protecting groups separately by means of two separate reactions.

For example, where $R^6$ represents a protecting group which can be removed by reduction, for example, a halogenated alkyl group, an aralkyl group or a benzhydryl group, the compound of formula (III) is contacted with a reducing agent; different reducing agents are preferred, depending upon the nature of tne protecting group. Where the carboxy-protecting group is a halogenated alkyl group (e.g. a 2,2-dibromoethyl or 2,2,2-trichloroethyl group), a preferred reducing agent is zinc with acetic acid. When the protecting group is an aralkyl group (for example a benzyl or p-nitrobenzyl group) or a benzhydryl group, the reduction is preferably effected using a catalyst (such as palladium-on-charcoal) or using an alkali metal sulphide (such as sodium sulphide or potassium sulphide). These reactions are preferably effected in the presence of a solvent, the nature of which is not critical, provided that it does not adversely affect the reaction. Preferred solvents include: alcohols, such as methanol or ethanol; ethers, such as tetrahydrofuran or dioxane; fatty acids, such as acetic acid; and mixtures of one or more of these organic solvents with water. The reaction is preferably effected at a relatively low temperature, for example, from 0° C. to ambient temperature. The time required for the reaction will vary, depending upon the nature of the starting materials and the reducing agents, but usually a period of from 5 minutes to 12 hours will suffice.

After completion of the reaction, the desired compound may be recovered from the reaction mixture by conventional means. For example, one suitable recovery procedure comprises filtering off insolubles, washing the remaining aqueous phase with a water-immiscible organic solvent and finally distilling off the water to give the desired product. This product may, if necessary, be further purified by such conventional techniques as recrystallization, preparative thin layer chromatography or column chromatography.

Where $R^5$ represents a protected alpha-hydroxyalkyl group, the protecting group may be removed prior to, simultaneously with or after removal of any carboxy-protecting group represented by $R^6$ and the nature and sequence of any elimination reaction or reactions will depend upon the nature of the respective protecting groups.

Where the group represented by $R^5$ is a lower aliphatic acyloxyalkyl group, such as an acetoxyalkyl group, the acyl group can be removed by contacting the compound with a base in the presence of an aqueous solvent. The nature of the solvent employed is not critical and any solvent commonly used for hydrolysis reactions may equally be used for this reaction. We prefer to use water or a mixture of water with an organic solvent, such as an alcohol (e.g. methanol, ethanol or propanol) or an ether (e.g. tetrahydrofuran or dioxane). The base employed is not particularly critical, although care should be taken to use a compound which does not affect other parts of the compound, particularly the beta-lactam ring. Preferred bases are alkali metal carbonates, particularly sodium carbonate or potassium carbonate. The reaction temperature is not critical, although a relatively low temperature, e.g. from 0° C. to ambient temperature, is preferred, in order to control side reactions. The time required for the reaction will vary, depending upon the nature of the starting materials and upon the reaction temperature, but a period of from 1 to 6 hours will normally suffice.

Where the group represented by $R^5$ is an alpha-aralkyloxycarbonyloxyalkyl group, such as a benzyloxycarbonyloxyalkyl or p-nitrobenzyloxycarbonyloxyalkyl group, the aralkyloxycarbonyl protecting group may be eliminated by contacting the compound with a reducing agent. Examples of reducing agents and reaction conditions which may be employed for this reaction are the same as those given above for the removal of a carboxy-protecting group $R^6$, where that group is an aralkyl group; accordingly, where $R^6$ represents an aralkyl group and $R^5$ represents an aralkyloxycarbonyloxyalkyl group, the two protecting groups may be removed simultaneously by this reaction.

Where the group represented by $R^5$ is a trialkylsilyloxyalkyl group, for example a t-butyldimethylsilyloxyalkyl group, the trialkylsilyl protecting group can be removed by treating the compound with tetrabutylammonium fluoride. The reaction is preferably effected in the presence of a solvent, the nature of which is not critical, provided that it has no adverse effect upon the reaction; suitable solvents are ethers such as tetrahydrofuran or dioxane. The reaction is preferably effected at aoout ambient temperature and will normally require from 10 to 18 hours.

Other protecting groups may similarly be removed by reactions well known in the art.

After completion of these reactions, the desired product may be recovered from the reaction mixture by conventional means and, if necessary, may be further purified by such conventional techniques as recrystallization, preparative thin layer chromatography or column chromatography.

The compound of formula (II) used as a starting material in the above reaction scheme is a novel compound and may be prepared from known compounds by either of the following Preparative methods Preparative Method (i)

As illustrated by the following reaction scheme:

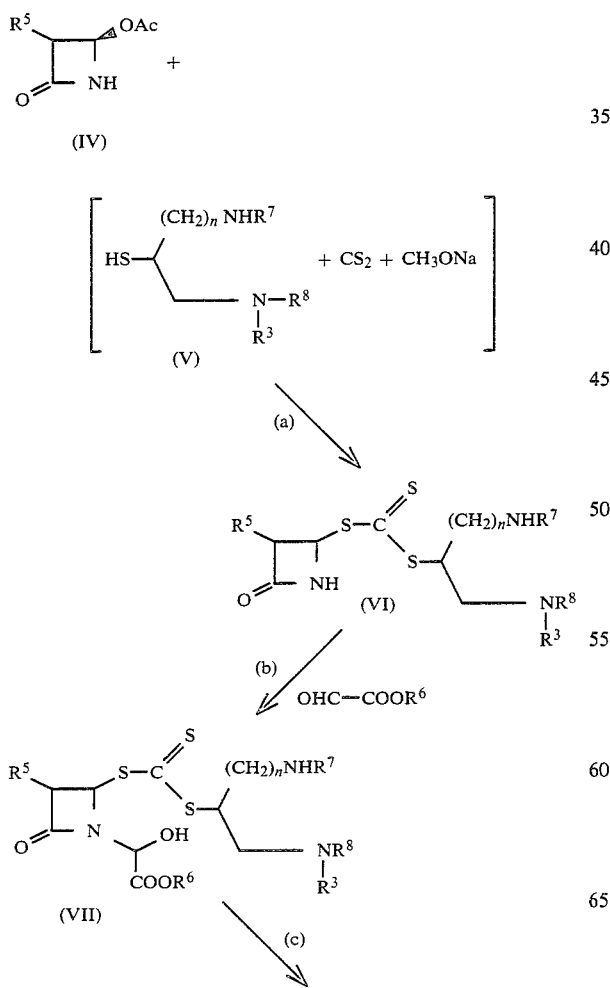

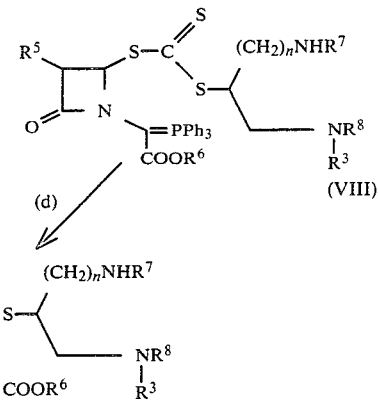

In the above formulae, $R^5$, $R^6$, $R^7$, and $R^8$ and n are as defined above, whilst Ac represents an acetyl group and Ph represents a phenyl group.

Step (a) comprises reacting a mercaptane of formula (V) with an equimolar amount of sodium methoxide in methanol, reacting the resulting product with carbon disulphide and then reacting the product of this reaction with the compound of formula (IV).

Step (b) comprises reacting the resulting compound of formula (VI) with glyoxylic acid or an ester thereof, to give the compound of formula (VII). This reaction may be effected in a solvent in a conventional manner.

Step (c) comprises reacting the resulting compound of formula (VII) with thionyl chloride or thionyl bromide in the presence of a base and then reacting the product with triphenylphosphine; again, this reaction is carried out in the presence of a solvent in a conventional matter.

Step (d) comprises heating the resulting compound of formula (VIII) to give the desired compound of formula (II). This reaction may be carried out in the presence of a solvent under conditions conventional for Wittig reactions.

Preparative Method (ii)

Compounds of formula (II) may also be prepared by reacting a compound of formula (IX) with a compound of formula (X), as illustrated below:

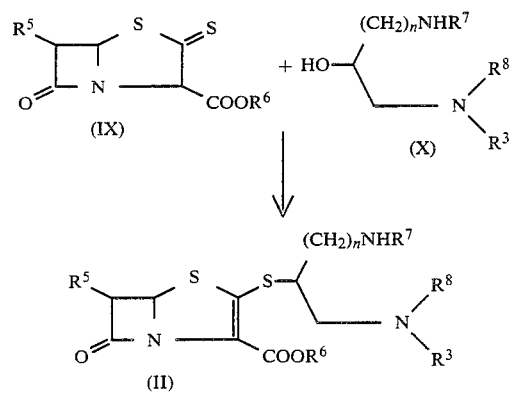

In the above formulae, $R^3$, $R^5$, $R^6$, $R^7$, $R^8$ and n are as defined above.

The reaction is preferably effected in the presence of triphenylphosphine and of diethyl azodicarboxylate in the presence of a solvent in a conventional manner.

Method B

The compounds of the invention may also be prepared as illustrated by the following reaction:

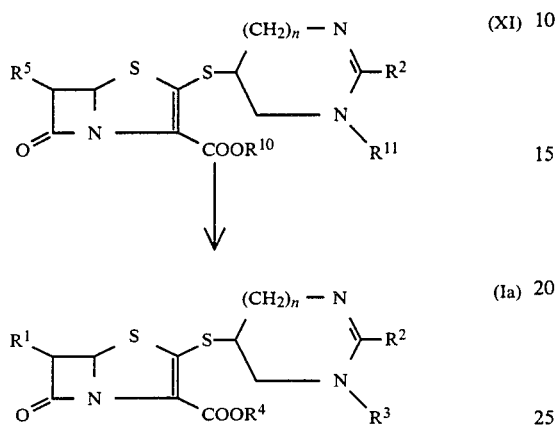

In the above formulae, $R^1$, $R^2$, $R^3$, $R^4$, $R^5$, and n are as defined above: $R^{10}$ represents a carboxy-protecting group; and $R^{11}$ represents an alkyl group or an amino-protecting group.

Examples of amino-protecting groups which may be represented by $R^{11}$ are as illustrated in relation to the groups represented by $R^7$ and $R^8$ and the methods employed for removing this group are as described for the first part of step (a) of Method A. Similarly, examples of carboxy-protecting groups which may be represented by $R^{10}$ have been given in relation to the group represented by $R^6$ and methods of removing such groups have been given in step (b) of Method A.

The compound of formula (XI) is a novel compound and may be prepared, for example, by Preparative Method (iii).

Preparative Method (iii)

The compound of formula (XI) may be prepared as illustrated by the following reaction scheme:

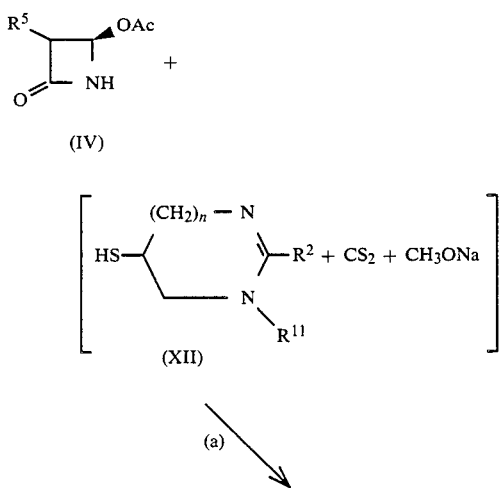

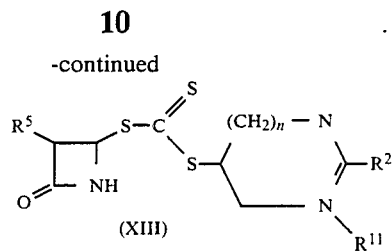

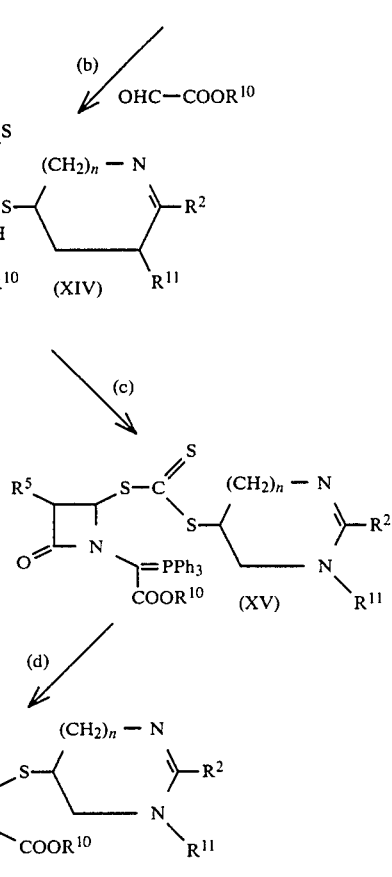

In the above formulae, $R^2$, $R^5$, $R^{10}$, $R^{11}$, n, Ac and Ph are as hereinbefore defined. Steps (a) to (d) of this reaction scheme correspond to and may be carried out under the same conditions as (a) to (d) of Preparative Method (i).

The compounds of the invention have been found to exhibit excellent antibacterial activity, comparable with that of the well known and extremely potent antiobiotic, thienamycin. The compounds exhibit their activity against both gram-positive microorganisms, such as *Staphylococcus aureus* or *Bacillus subtilis*, and gram-negative microorganisms, such as *Escherichia coli*, *Shigella flexneri*, *Klebsiella pneumoniae*, *Proteus vulgaris*, *Pseudomonas aeruginosa* and species of *Serratia* and *Enterobacter*.

The activities of certain of the compounds of the invention against various bacteria, in terms of their minimal inhibitory concentrations (microg/ml), determined by the agar plate dilution method, are shown in the following Table. The compounds of the invention are identified as follows:

Compound A: (5R, 6S)-6-[1-(R)-hydroxyethyl]-2-(3,4,5,6-tetrahydropyrimidin-5-ylthio)penem-3-carboxylic acid:

Compound B: (5R,6S)-6-[1-(R)-hydroxyethyl]-2-(2-methyl-3,4,5,6-tetrahydropyrimidin-5-ylthio)penem-3-carboxylic acid.

As a control, similar tests were carried out against the known antibiotic, thienamycin, and the results of these tests are also shown in the following Table.

TABLE

| Microorganism | A | B | thienamycin |
|---|---|---|---|
| *Staphylococcus aureus* 209 P | ≦0.01 | ≦0.01 | ≦0.01 |
| *Staphylococcus aureus* 56 | ≦0.01 | ≦0.01 | ≦0.01 |
| *Escherichia coli* NIHJ | 0.2 | 0.2 | 0.1 |
| *Escherichia coli* 609 | 0.2 | 0.2 | 0.1 |
| *Shigella flexneri* 2a | 0.2 | 0.2 | 0.1 |
| *Psuedomonas aeruginosa* | 3.1 | 6.2 | 6.2 |
| *Klebsiella pneumoniae* 806 | 0.4 | 0.2 | 0.1 |
| *Klebsiella pneumoniae* 846 | 0.4 | 0.2 | 0.1 |
| *Proteus vulgaris* | 6.2 | 3.1 | 3.1 |
| *Salmonella enteritidis* G | 0.4 | 0.2 | 0.2 |

Accordingly, the compounds of the invention are useful for the treatment of diseases caused by these pathogenic microorganisms. They can be administered for this purpose orally, for example in the form of tablets, capsules, granules, powders or syrups, or parenterally, for example through intervenous or intramuscular injections. The dose will vary, depending upon the age, body weight and condition of the patient and on the form and times of administration; however, in general, the adult daily dose would be from 200 to 3000 mg of the compound, which may be administered in a single dose or in divided doses.

The preparation of certain of the compounds of the invention is further illustrated by the following Examples, whilst tne preparation of certain starting materials is illustrated in the following Preparations.

EXAMPLE 1

(5R,6S)-6-[1-(R)-Hydroxyethyl]-2-(3,4,5,6-tetrahydropyrimidin-5-ylthio)penem-3-carboxylic acid 30mg of p-nitrobenzyl (5R,6S)-2-[1,3-bis(p-nitrobenzyloxycarbonylamino)propan-2-ylthio]-6-[1-(R)-hydroxyethyl]penem-3-carboxylate were dissolved in 5 ml of tetrahydrofuran. To this solution were added 5 ml of a phosphate buffer having a pH of 7.1 and 60 mg of 10% w/w palladium-on-charcoal. The mixture was then stirred in a stream of hydrogen at room temperature for 3 hours, after which it was left to stand overnight at room temperature. The catalyst was filtered off using a Celite (trade mark) filter aid. The filtrate was washed twice with ethyl acetate and then concentrated to about 5 ml by evaporation under reduced pressure. This aqueous residue was ice-cooled and adjusted to a pH value of 8.5 by the addition of a 0.5N aqueous solution of sodium hydroxide. 17 mg of methyl formimidate hydrochloride were added to the resulting solution. The mixture was adjusted to a pH value of 8.5 by the addition of an aqueous solution of sodium hydroxide, stirred under ice-cooling for 10 minutes, adjusted to a pH value of 7.0 by the addition of 0.5N hydrochloric acid and subjected to column chromatography through Diaion (trade mark) HP20AG, eluted with 10% v/v aqueous acetone, to give 2.1 mg of the desired compound as a colourless powder.

Infrared absorption spectrum $\nu_{max}$(KBr) cm$^{-1}$: 3400, 1765, 1670, 1590.

Nuclear magnetic resonance spectrum (D$_2$O) δppm: 1.32 (3H, doublet, J=6.0 Hz); 3.2–3.8 (5H, multiplet); 3.95 (1H, doubled doublet, J=8.0 and 2.0 Hz); 4.1–4.4 (1H, multiplet); 5.72 (1H, doublet, J=2.0 Hz); 8.00 (1H, singlet).

EXAMPLE 2

(5R,6S)-2-(2-Cyanometnyl-3,4,5,6-tetrahydropyrimidin-5-ylthio)-6-[1-(R)-hydroxyethyl]penem-3-carboxylic acid Following the procedure of Example 1, the desired compound was obtained as a colourless powder from 30 mg of p-nitrobenzyl (5R,6S)-2-[1,3-bis-(p-nitrobenzyloxycarbonylamino)propan-2-ylthio]-6-[1-(R)-hydroxyethyl]penem-3-carboxylate and 25 mg of methyl cyanoacetoimidate.

Infrared absorption spectrum $\nu_{max}$(KBr) cm$^{-1}$: 3400, 2300, 1760, 1660, 1600.

EXAMPLE 3

(5R,6S)-6-[1-(R)-Hydroxyethyl]-2-(2-methyl-3,4,5,6-tetrahydropyrimidin-5-ylthio)penem-3-carboxylic acid 850 mg of p-nitrobenzyl (5R,6S)-2-[1,3-bis(p-nitrobenzyloxycarbonylamino)propan-2-ylthio]-6-[1-(R)-hydroxyethyl]penem-3-carboxylate were dissolved in 140 ml of tetrahydrofuran. To the resulting solution were added 140 ml of a phosphate buffer (pH 7.0) and 425 mg of platinum oxide. The mixture was stirred under a stream of hydrogen gas at room temperature for 3.5 hours. The catalyst was then filtered off under reduced pressure and the filtrate was concentrated to one-half of its original volume and washed twice with ethyl acetate. The aqueous solution was ice-cooled and adjusted to a pH value of 8.5 by the addition of a dilute aqueous solution of sodium hydroxide. 1.25 g of ethyl acetimidate hydrochloride were added and the resulting mixture was stirred under ice-cooling for 15 minutes, whilst the pH of the mixture was adjusted to a value of 8.5. The pH of the mixture was then adjusted to a value of 7.0 by the addition of dilute hydrochloric acid and the mixture was subjected to column chromatography through Diaion HP 20AG, eluted with 10% v/v aqueous acetone, to obtain 150 mg of the desired compound as a colourless powder.

Ultraviolet absorption spectrum $\lambda_{max}$(H$_2$O)$_{nm}$(ε): 257.9 (4920), 320.7 (6000).

Infrared absorption spectrum $\nu_{max}$(KBr)cm$^{-1}$: 3400, 1770, 1660, 1590.

Nuclear magnetic resonance spectrum (D$_2$O) δppm; 1.33 (3H, doublet, J=6.5 Hz); 2.24 (3H, singlet); 3.4–4.1 (6H,multiplet); 4.15–4.4 (1H, multiplet); 5.76 (1H, doublet J=2.0 Hz).

PREPARATION 1

(3S,4R)-3-[1-(R)-t-butyldimethylsilyloxyethyl]-4-[[(1,3-bis(p-nitrobenzyloxycarbonylamino)propan-2-ylthio)-thiocarbonyl]thio]azetidin-2-one 5.3 g of 2-acetylthio-1,3-bis(p-nitrobenzyloxycarbonylamino)propane in a mixture of 161 ml of methanol and 40 ml of tetrahydrofuran were cooled to −20° C. To the solution were added 9.95 ml of a methanolic solution of sodium methoxide containing 1 mM of sodium methoxide per 1 ml of methanol. The mixture was stirred at −10° to −15° C. for 30 minutes, after which it was mixed with 0.961 ml of carbon disulphide and stirred at −20° C. for 15 minutes. Then 20 ml of a methanolic solution containing 3.59 g of 4-acetoxy-3-[1-(R)-t-butyldimethylsilyloxyethyl)-2-azetidinone was added to the above mixture and stirred at −20° C. for 1 hour.

The mixture was cooled to −50° C. and then poured into a mixture of .20 ml of acetic acid and 200 ml of water. The mixture was extracted with ethyl acetate. The extract was washed with a saturated aqueous solution of sodium chloride and dried over anhydrous sodium sulphate. The solvent was distilled off and the residue was subjected to medium pressure column chromatography througn silica gel, eluted with 3:1–2:1 by volume mixtures of benzene and ethyl acetate, to give 6.1 g of the desired compound.

Nuclear Magnetic Resonance spectrum (CDCl$_3$) δppm: 0.10 (6H, singlet); 0.90 (9H, singlet); 1.22 (3H, doublet, J=6.0 Hz); 3.1–3.8 (6H, multiplet); 4.1–4.5 (1H, multiplet); 5.21 (4H, singlet); 5.65 (1H, doublet, J=2.0 Hz); 5.98 (2H, broad singlet); 7.20 (1H, broad singlet); 7.51, 8.19 (8H, A$_2$B$_2$, J=9.0 Hz).

PREPARATION 2 p-Nitrobenzyl 2-[(3S,4R)-3-1-(R)-t-butyldimethylsilyloxyethyl]-4-[[(1,3-bis(p-nitrobenzyloxycarbonylamino)propan-2-ylthio)thiocarbonyl]thio-2-oxo-1-azetidinyl]-2-hydroxyacetate A mixture of 6.1 g of (3S,4R)-3-[1-(R)-t-butyldimethylsilyloxyethyl]-4-[[(1,3-bis(p-nitrobenzyloxycarbonylamino)propan-2-ylthio)thiocarbonyl]-thio)azetidin-2-one and 2.7 g of p-nitrobenzyl glyoxylate hydrate in 180 ml of benzene was heated under reflux for 2.5 hours. After completion of the reaction, the solvent was distilled off and the residue was subjected to medium pressure column chromatography through silica gel, eluted with a 1:1 by volume mixture of benzene and ethyl acetate, to give 6.2 g of the desired compound (a mixture of configuration isomers due to the hydroxy group) as an amorphous powder.

Nuclear Magnetic Resonance spectrum (CDCl$_3$) δppm: 0.05 (3H, singlet); 0.08 (3H, singlet); 0.87 (9H, singlet); 1.20 (3H, doublet, J=6.0 Hz); 3.3–3.8 (5H, multiplet); 4.1–4.5 (3H, multiplet); 4.8 (1H,broad singlet); 5.22–5.20 (6H, multiplet); 5.68 (1H, multiplet); 5.80 (2H, broad singlet); 7.51, 8.19 (12H, A$_2$B$_2$, J=8.4 Hz).

PREPARATION 3 p-Nitrobenzyl 2-[(3S,4R)-3-[1-(R)-t-butyldimethylsilyloxyethyl]-4-[[(1,3-bis(p-nitrobenzyloxycarbonylamino)propan-2-ylthio)thiocarbonyl]thio]-2-oxo-1-azetidinyl]-2-(triphenylphosphoranylidene)acetate 6.1 of p-nitrobenzyl 2-[3S,4R)-3-[(R)-1-t-butyldimethylsilyloxyethyl]-4-[[(1,3-bis(p-nitrobenzyloxycarbonylamino)propan-2-ylthio) thiocarbonyl]thio]-2-oxo-1-azetidinyl]-2-hydroxyacetate were dissolved in 80 ml of tetrahydrofuran. To this solution were added successively 0.795 ml of 2,6-lutidine and 0.474 ml of thionyl chloride at −20° C. The mixture was then stirred at the same temperature for 15 minutes. A further 1.44 ml of 2,6-lutidine and 3.27 g of triphenylphosphine were added to the mixture. The resulting mixture was then gently heated under reflux in a stream of nitrogen gas for 48 hours. After completion of the reaction, the reaction mixture was concentrated by evaporation under reduced pressure and the residue was extracted with ethyl acetate. The extract was washed successively with water, an aqueous solution of sodium bicarbonate and a saturated aqueous solution of sodium chloride and dried over anhydrous sodium sulphate. The solvent was distilled off and the residue was subjected to medium pressure column chromatography through silica gel, eluted with 4:1–1:1 by volume mixtures of benzene and ethyl acetate, to obtain 2.7 g (35.4%) of the desired compound.

Infrared absorption spectrum ν$_{max}$(CHCl$_3$) cm$^{-1}$: 1755, 1705.

PREPARATION 4 p-Nitrobenzyl (5R,6S)-6-[1-(R)-t-butyldimethylsilyoxyethyl]-2-[1,3-bis(p-nitrobenzyloxycarbonylamino)propan-2-ylthio]-penem-3-carboxylate and its (5S) isomer A solution of 2.7 g of p-nitrobenzyl 2-[(3S,4R)-3-[1-(R)-t-butyldimethylsilyloxyethyl]-4-[[(1,3-bis(p-nitrobenzyloxycarbonylamino)propan-2-ylthio)thiocarbonyl]thio]-2-oxo-1-azetidinyl]-2-(triphenylphosphoranylidene)acetate and 65 mg of hydroquinone in 125 ml of xylene was heated under a stream of nitrogen gas at 130° C. for 20 hours. After completion of the reaction, the solvent was distilled off under reduced pressure and the residue was subjected to Lobar column chromatography through silica gel eluted with a 1:1 by volume mixture of benzene and ethyl acetate, to give 1.50 g of the desired (5R) isomer and 0.54 g of the (5S) isomer, quantitatively.

(5R) Isomer

Nuclear Magnetic Resonance spectrum (CDCl$_3$) δppm: 0.06 (3H, singlet); 0.09 (3H, singlet); 0.83 (9H, singlet); 1.24 (3H, doublet, J=6.0 Hz); 3.3–3.7 (5H, multiplet); 3.75 (1H, doubled doublet, J=3.4 and 1.5 Hz); 4.1–4.4 (1H, multiplet); 5.18 (4H, singlet); 5.13, 5.38 (2H, AB-quartet, J=13.2 Hz); 5.65 (1H, doublet J=1.5 Hz); 5.7–6.05 (2H, broad singlet; 7.45, 8.12 (8H, A$_2$B$_2$, J=8.7 Hz); 7.56, 8.12 (4H, A$_2$B$_2$, J=8.7 Hz).

(5S) Isomer

Nuclear Magnetic Resonance spectrum (CDCl$_3$) δppm: 0.12 (6H, singlet); 0.86 (9H, singlet); 1.30 (3H, doublet, J=6.0 Hz); 3.38–3.68 (2H, multiplet); 3.95–4.40 (5H, multiplet); 5.15 (4H, singlet); 5.13, 5.41 (2H, AB-quartet, J=14.4 Hz); 5.65 (1H, doublet, J=3.6 Hz); 7.10 (2H, broad singlet); 7.43, 8.15 (8H, A$_2$B$_2$, J=9.0 Hz); 7.55, 8.15 (4H, A$_2$B$_2$, J=8.7 Hz).

PREPARATION 5 p-Nitrobenzyl (5R,6S)-6-[1-(R)-hydroxyethyl])-2-[1,3-bis-(p-nitrobenzyloxycarbonylamino)propan-2-ylthio]penem-3-carboxylate To a solution of 113 mg of p-nitrobenzyl (5R,6S)-6-[1-(R)-t-butyldimethylsilyloxyethyl]-2-[1,3-bis(p-nitrobenzyloxycarbonylamino)propan-2-ylthio]penem-3-carboxylate in 2 ml of tetrahydrofuran were added 0.074 ml of acetic acid and 162 mg of tetrabutylammonium fluoride. The mixture was left to stand at 28° C. for 16 hours and tnen diluted with ethyl acetate and washed successively with a saturated aqueous solution of sodium chloride, a 5% w/v aqueous solution of sodium bicarbonate and a saturated aqueous solution of sodium chloride. The solvent was distilled off and the residue was subjected to medium pressure column chromatography through silica gel, eluted with ethyl acetate, to give 91 pl mg (91.9%) of the desired compound.

Nuclear Magnetic Resonance spectrum (CDCl$_3$) δppm; 1.30 (3H, doublet, J=6.0 Hz); 3.3–3.7 (6H, multiplet); 4.0–4.4 (1H, multiplet); 5.15 (4H, singlet); 5.11, 5.37 (2H, AB-quartet, J=13.5 Hz); 5.61 (1H, doublet, J=1.5 Hz); 5.7–6.0 (2H, broad singlet); 7.42, 8.10 (8H, $A_2B_2$, J=8.7 Hz); 7.52, 8.10 (4H, $A_2B_2$, J=8.10 Hz).

PREPARATION 6 p-Nitrobenzyl (5S,6S)-6-[1-(R)-t-butyldimethyl-silyloxyethyl]-2-[1,3-bis(p-nitrobenzyloxycarbonylamino)-propan-2-ylthio]-penem-3-carboxylate To a solution of 396 mg of triphenylphosphine in 6 ml of tetrahydrofuran were added 0.238 ml of diethyl azodicarboxylate, after which the mixture was stirred for 10 minutes. Meanwhile, 678 mg of, 1,3-bis(p-nitrobenzyloxycarbonylamino)-2-hydroxypropane and 500 mg of p-nitrobenzyl (5S,6S)-6-[1-(R)-t-butyldimethylsilyloxyethyl]-2-thioxopenam-3-carboxylate were dissolved in 10 ml of tetrahydrofuran. The solution thus obtained was added dropwise to the mixture obtained above, whilst ice-cooling. The resulting mixture was stirred at the same temperature for 15 minutes and then at room temperature for 4 hours, after which it was extracted with ethyl acetate. The extract was washed with a saturated aqueous solution of sodium chloride and then dried over anhydrous sodium sulphate. The solvent was distilled off and the residue was subjected to medium pressure column chromatography through silica gel, eluted with a 2:1 by volume mixture of benzene and ethyl acetate, to give 246 mg (26.3%) of the desired compound.

Nuclear Magnetic Resonance spectrum ($CDCl_3$) δppm: 0.12 (6H, singlet); 0.86 (9H, singlet); 1.30 (3H, doublet, J=6.0 Hz); 3.38–3.68 (2H, multiplet); 3.95–4.40 (5H, multiplet); 5.15 (4H, singlet); 5.13, 5.41 (2H, AB-quartet, J=14.4 Hz); 5.65 (1H, doublet, J=3.6 Hz); 7.10 (2H, broad singlet); 7.43, 8.15 (8H, $A_2B_2$, J=9.0 Hz); 7.55, 8.15 (4H, $A_2B_2$, J=8.7 Hz).

We claim:

1. A compound of formula (I):

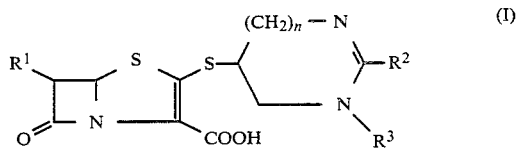

wherein:
 $R^1$ represents a $C_1$–$C_4$ alkyl group or a $C_1$–$C_3$ alpha-hydroxyalkyl group;
 $R^2$ represents a hydrogen atom, an alkyl group, a cycloalkyl group or an alkyl group having at least one substituent selected from $C_1$–$C_4$ alkoxy groups, cyano groups, alkoxycarbonyl groups and halogen atoms;
 $R^3$ represents a hydrogen atom or an alkyl group; and
 n is 1 or 2;
and pharmaceutically acceptable salts and esters thereof.

2. Compounds as claimed in claim 1, wherein:
 $R^1$ represents a $C_2$ or $C_3$ alpha-hydroxyalkyl group;
 $R^2$ represents a hydrogen atom, a $C_1$–$C_3$ alkyl group or a ($C_1$–$C_2$ alkoxy)-($C_1$–$C_2$ alkyl) group;
 $R^3$ represents a hydrogen atom or a $C_1$–$C_4$ alkyl group; and
 n is 1.

3. The compound as claimed in claim 1, wherein:
 $R^1$ represents a 1-hydroxyethyl group;
 $R^2$ represents a hydrogen atom or a methyl, ethyl or methoxyxethyl group;
 $R^3$ represents a hydrogen atom or a methyl group; and
 n is 1.

4. The compound as claimed in claim 1, wherein the configuration of said compounds is the (5R,6S) configuration and, where $R^1$ represents an alphahydroxyalkyl group, the configuration of the hydroxy group thereof is the R configuration.

5. The compound as claimed in any one of claims 1 to 4, wherein said ester is a lower aliphatic acyloxymethyl, lower 1-alkoxycarbonyloxyethyl or (5-methyl-2-oxo-1,3-dioxolen-4-yl)methyl ester.

6. The compound as claimed in claim 1, selected from the group consisting of 6-(1-hydroxyethyl)-2-(3,4,5,6-tetrahydropyrimidin-5-ylthio)penem-3-carboxylic acid, 2-(2-ethyl-3,4,5,6-tetrahydropyrimidin-5-ylthio)penem-3-carboxylic acid, 2-(2-ethyl-3,4,5,6-tetrahydropyrimidin-5-ylthio)-6-(1-hydroxyethyl)penem-3-carboxylic acid, 6-(1-hydroxyethyl)-2-(2-methoxymethyl-3,4,5,6-tetrahydropyrimidin-5-ylthio)penem-3-carboxylic and pharmaceutically acceptable salts thereof.

7. A pharmaceutical composition comprising an antibiotic agent in admixture with a pharmaceutically acceptable carrier or diluent, wherein said agent is selected from the group consisting of compounds of formula (I):

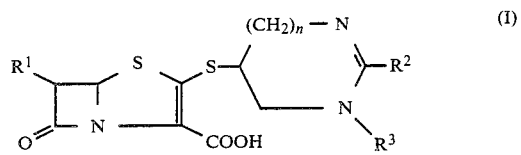

wherein:
 $R^1$ represents a $C_1$–$C_4$ alkyl group or a $C_1$–$C_3$ alpha-hydroxyalkyl group;
 $R^2$ represents a hydrogen atom, an alkyl group, a cycloalkyl group or an alkyl group having at least one substituent selected from $C_1$–$C_4$ alkoxy groups, cyano groups, alkoxycarbonyl groups and halogen atoms;
 $R^3$ represents a hydrogen atom or an alkyl group; and
 n is 1 or 2
and pharmaceutically acceptable salts and esters thereof.

8. A pharmaceutical composition as claimed in claim 7, wherein:
 $R^1$ represents a $C_2$ or $C_3$ alpha-hydroxyalkyl group;
 $R^2$ represents a hydrogen atom, a $C_1$–$C_3$ alkyl group or a ($C_1$–$C_2$ alkoxy)-($C_1$–$C_2$ alkyl) group;
 $R^3$ represents a hydrogen atom or a $C_1$–$C_4$ alkyl group; and
 n is 1.

9. A pharmaceutical composition as claimed in claim 7, wherein:
 $R^1$ represents a 1-hydroxyethyl group;
 $R^2$ represents a hydrogen atom or a methyl, ethyl or methoxymethyl group;
 $R^3$ represents a hydrogen atom or a methyl group; and
 n is 1.

10. The pharmaceutical composition as claimed in claim 7, wherein the configuration of said compounds is the (5R,6S) configuration and, where $R^1$ represents an alpha-hydroxyalkyl group, the configuration of the hydroxy group thereof is the R configuration.

11. The pharmaceutical composition as claimed in any one of claims 7 to 10, wherein said ester is a lower aliphatic acyloxymethyl, lower 1-alkoxycarbonyloxyethyl or (5-methyl-2-oxo-1,3-dioxolen-4-yl)methyl ester.

12. The pharmaceutical composition as claimed in claim 7, wherein said agent is selected from the group consisting of 6-(1-hydroxy-ethyl)-2-(3,4,5,6-tetrahydropyrimidin-5-ylthio)penem-3-carboxylic acid and pharmaceutically acceptable salts thereof.

13. The pharmaceutical composition as claimed in claim 7, wherein said agent is selected from the group consisting of 6-(1-hydroxyethyl)-2-(2-methyl-3,4,5,6-tetrahydropyrimidin-5-ylthio)penem-3-carboxylic acid and pharmaceutically acceptable salts thereof.

14. The pharmaceutical composition as claimed in claim 7, wherein said agent is selected from the group consisting of 2-(2-ethyl-3,4,5,6-tetrahydropyrimidin-5-ylthio)-6-(1-hydroxyethyl)penem-3-carboxylic acid and pharmaceutically acceptable salts thereof.

15. The pharmaceutical composition as claimed in claim 7, wherein said agent is selected from the group consisting of 6-(1-hydroxyethyl)-2-(2-methoxymethyl-3,4,5,6-tetrahydropyrimidin-5-ylthio)penem-3-carboxylic acid and pharmaceutically acceptable salts thereof.

16. The compound as claimed in claim 1, selected from the group consisting of 6-(1-hydroxyethyl)-2-(2-methyl-3,4,5,6-tetrahydropyrimidin-5-ylthio)penem-3-carboxylic acid and pharmaceutically acceptable salts thereof.

17. The compound as claimed in claim 1, selected from the group consisting of 2-(2-ethyl-3,4,5,6-tetrahydropyrimidin-5-ylthio)-6-(1-hydroxyethyl)penem-3-carboxylic acid and pharmaceutically acceptable salts thereof.

18. The compound as claimed in claim 1, selected from the group consisting of 6-(1-hydroxyethyl)-2-(2-methoxymethyl-3,4,5,6-tetrahydropyrimidin-5-ylthio)-penem-3-carboxylic acid and pharmaceutically acceptable salts thereof.

* * * * *

UNITED STATES PATENT AND TRADEMARK OFFICE
CERTIFICATE OF CORRECTION

PATENT NO. : 4,613,595
DATED : September 23, 1986
INVENTOR(S) : MIYADERA et al

It is certified that error appears in the above-identified patent and that said Letters Patent is hereby corrected as shown below:

Column 15, line 61 (Claim 2), change "Compounds to --The compound--.

Column 16, lines 19-23 (Claim 6), delete "5-ylthio)... carboxylic".

Column 16, line 48 (Claim 7), after "1 or 2", insert --;--.

Column 16, line 51 (Claim 8), change "A" to --The--.

Column 16, line 59 (Claim 9), change "A" to --The--.

Signed and Sealed this

Twelfth Day of January, 1993

Attest:

DOUGLAS B. COMER

*Attesting Officer*          *Acting Commissioner of Patents and Trademarks*